United States Patent [19]

Karle

[11] Patent Number: 4,459,936

[45] Date of Patent: Jul. 17, 1984

[54] APPARATUS FOR INDICATING WHETHER THE INTERIOR OF A CONTAINER HAS BEEN STERILIZED DURING A STERILIZATION PROCESS

[75] Inventor: David A. Karle, McKean, Pa.

[73] Assignee: American Sterilizer Company, Erie, Pa.

[21] Appl. No.: 373,650

[22] Filed: Apr. 30, 1982

[51] Int. Cl.³ .................... A61L 2/06; G01N 33/00
[52] U.S. Cl. ................................ 116/207; 422/26; 436/1
[58] Field of Search .................. 116/206, 207, 216; 374/162; 422/57, 58, 26; 436/1; 435/31, 39

[56] References Cited

U.S. PATENT DOCUMENTS

| | | | |
|---|---|---|---|
| 2,222,067 | 11/1940 | Chaney et al. | 116/216 X |
| 2,856,885 | 10/1958 | Huyck et al. | 374/162 X |
| 3,093,242 | 6/1963 | Huyck et al. | 116/206 |
| 3,260,112 | 7/1966 | Godbey et al. | 116/216 X |
| 3,785,336 | 1/1974 | Roszkowski | 374/162 X |
| 3,955,420 | 5/1976 | Parker | 116/216 |
| 3,960,670 | 6/1976 | Pflug | 422/26 |
| 3,967,502 | 7/1976 | Moran | 374/102 |
| 3,991,881 | 11/1976 | Augurt | 116/206 X |
| 4,066,646 | 1/1978 | LeBlanc, Jr. et al. | 422/57 X |
| 4,195,058 | 3/1980 | Patel | 436/1 X |
| 4,272,478 | 6/1981 | Vihko | 422/57 |
| 4,289,088 | 9/1981 | Scibelli | 436/1 X |

Primary Examiner—Daniel M. Yasich
Attorney, Agent, or Firm—Robert D. Yeager; Andrew J. Cornelius

[57] ABSTRACT

Apparatus for indicating whether the contents of a container have been sterilized during a sterilization process including a first member having a portion for coacting with the sterilization agent to indicate the sterility of the contents of the container. A second member is adapted to extend into the interior of the container to be sterilized and receive and releasably engage the first member so that said first member can be positioned within the interior of the container to be sterilized during the sterilization process and so that the first member can be placed in and withdrawn from the second member without exposing the contents of the container to the surrounding environment or the operator to the contents of the container. At least a portion of the second member is selectively permeable to the sterilization agent so that the sterilization agent can come in contact with the coacting portion of the first member and yet prevent the coacting portion from being contaminated if the contents of the container have been incompletely sterilized.

4 Claims, 1 Drawing Figure

U.S. Patent    Jul. 17, 1984    4,459,936
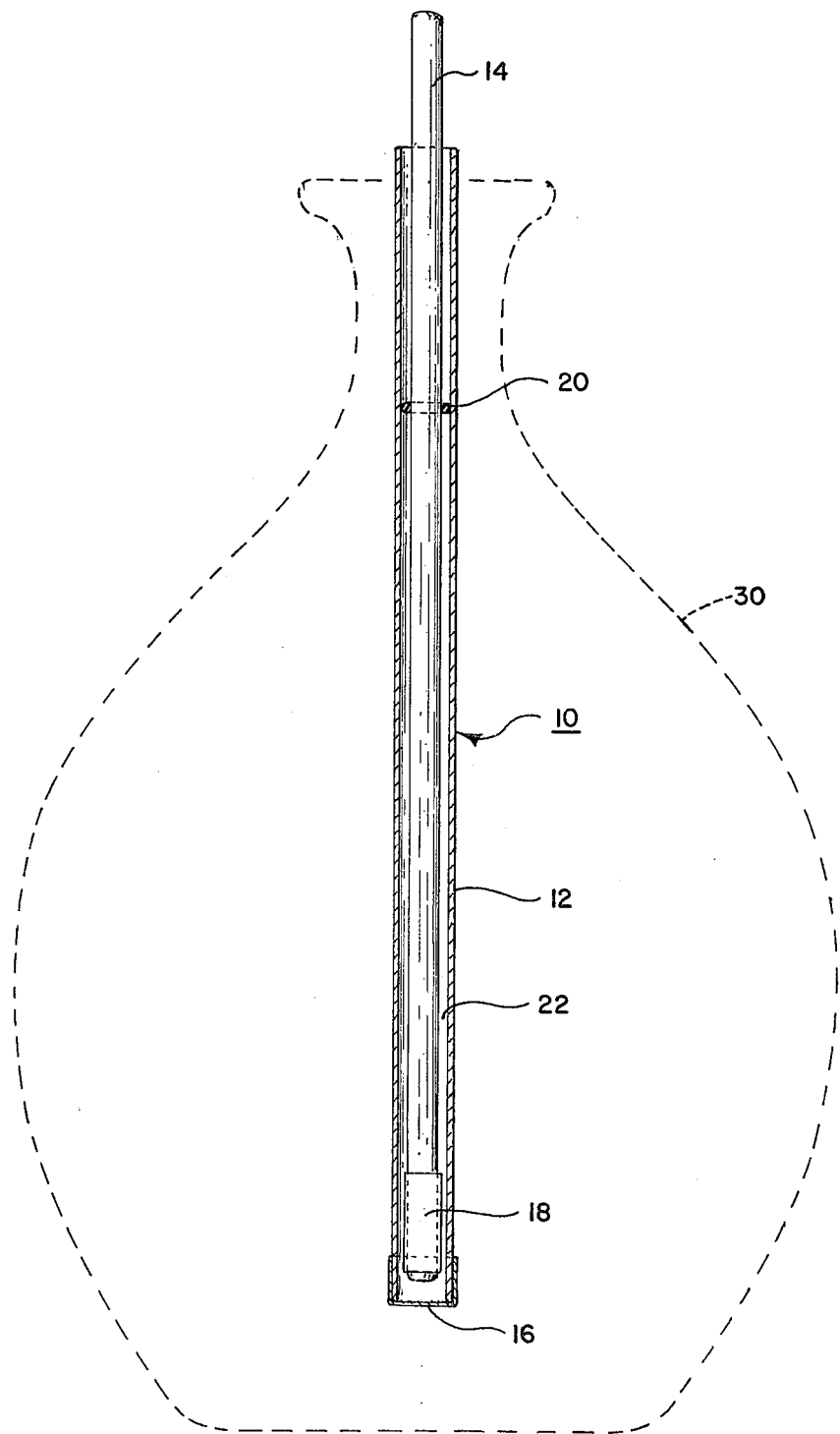

APPARATUS FOR INDICATING WHETHER THE INTERIOR OF A CONTAINER HAS BEEN STERILIZED DURING A STERILIZATION PROCESS

BACKGROUND OF THE INVENTION

1. Field of the Invention

The invention relates generally to apparatus for indicating whether the contents of a container have been sterilized during a sterilization process and more specifically to such apparatus wherein the user need not be exposed to contamination within the container while inserting the indicator within or retrieving the indicator from the container.

2. Description of the Prior Art

Workers in the art have developed many methods for determining whether goods have been sterilized by a sterilization process. The use of biological indicators involves incubating and observing a growth media that has been exposed to a sterilization process to determine whether the sterilization process was complete. Often an agent sensitive to bacteriological growth is used to signal the presence of colonies of bacteria. Chemical indicators are known wherein the sterilization agent reacts with the indicator to provide an observable change in the indicator. Thus, by observing the indicator one can determine whether the sterilization agent had been in contact with the indicator for a sufficient length of time to sterilize the goods.

Many devices have been developed to utilize the various indicators. One such device, as disclosed in U.S. Pat. No. 3,661,717, includes an ampul that contains an indicator nutrient medium and filter paper that is sensitive to bacteriological growth. After the indicator has been exposed to a sterilization cycle, the ampul is ruptured causing the nutrient medium to come in contact with the filter paper. The indicator is then incubated and observed to determine whether the sterilization process was complete.

Situations arise, as for example with biohazard waste, when the contents of a sterilized container must be shown to be sterile. In such situations, the indicator must be carefully placed within the container proximate the biohazard waste prior to the sterilization process and later retrieved for observation. Thus, if indicator devices such as those described above are used, the container must be opened to retrieve the indicator. Thus, the operator is exposed to the contents and the contents exposed to the environment. Moreover, if the sterilization process has not been completely effective, the indicator itself is a source of contamination to the user. Accordingly, if the biohazardous contents have not been sterilized as determined by the indicator, both the operator and environment will have been exposed to the risk of contamination.

U.S. Pat. No. 3,960,670, discloses an indicator device for steam sterilization process including apparatus for properly positioning the indicator with the container to be sterilized. However, in order to observe the indicator, the entire device must be removed from the container. Thus the interior of the container is exposed to the environment and the individual and indicator are exposed to the contents which may still be contaminated.

Accordingly, it is desired to have an indicator apparatus wherein the portion containing the indicator can be positioned within the container and retrieved from the container without exposing the contents of the container to the environment or the individual to the contents and without contaminating the indicator.

SUMMARY OF THE INVENTION

The present invention provides apparatus for indicating whether the contents of a container have been sterilized during a sterilization process. The device enables the user to place the portion of the apparatus containing the indicator within the container without exposing the contents of the container to the environment or the individual to the contents and without contaminating the indicator.

The apparatus of the present invention includes a first member, the first member having a portion for coacting with the sterilization agent to indicate the sterility of the contents of the container. A second member is adapted to extend into the interior of the container to be sterilized and receive and releasably engage the first member so that the coacting portion of the first member can be positioned within the interior of the container to be sterilized during the sterilization process and so that the first member can be placed in and withdrawn from the second member without exposing the operator to the contents or the contents of the container to the surrounding environment. At least a portion of the second member is selectively permeable to the sterilization agent so that the sterilization agent can come in contact with the coacting portion of the first member. In addition, the apparatus includes apparatus for preventing the sterilization agent from coming in contact with the coacting portion of the first member unless the sterilization agent has first permeated a portion of the second member, and as a result contacted the innermost contents of the container.

Preferably, the first member is an elongated cylindrical shaft having the coacting portion disposed at its lower end. The coacting portion may be releasably secured to the first member so that the coacting portion may be removed from the first member for observation and said first member may be fitted with another coacting portion, placed within another second member and used again.

Preferably, the second member is an elongated cylindrical shaft having a bore therethrough for receiving the first member and a septum disposed at its lower end that is selectively permeable to the sterilization agent. It should be noted that when sterilizing carcasses of laboratory animals for purposes of the present application, the carcass is considered both the container and the contents.

BRIEF DESCRIPTION OF THE FIGURE

The FIGURE is a view of the indicating apparatus according to the invention in position in a biohazard bag in a sterilization chamber.

DETAILED DESCRIPTION OF THE PREFERRED EMBODIMENT

With reference to the FIGURE, indicator apparatus, generally indicated by the reference numeral 10, includes outer shaft or member 12 and inner shaft or member 14. Indicator apparatus 10 is adapted for use with a sterilization container such as a biohazard bag 30 as shown by the dotted lines in FIG. 1 in a sterilization chamber.

Outer shaft 12 is hollow and has bore 22 which is adapted to receive inner shaft 14. Outer shaft 12 is formed of a material that is not permeable to the sterilization agent. However, outer shaft 12 includes septum 16 at its lower end. Septum 16 which is selectively permeable permits passage of the sterilization agent, but not biohazardous organisms, to the interior of shaft 12. The sterilization agent may be any known medium commonly used in sterilization processes such as heat, steam or ethylene oxide.

Inner shaft 14 includes a coating portion 18 that contains an indicator. The indicator may be any commonly known indicator such as a biological or chemical agent that provides an observable signal when it has been in contact with the sterilization agent for a sufficient period of time to be sterilized. Portion 18 may be releasably secured to the lower end of inner shaft 14.

Seal 20 is disposed between outer shaft 12 and inner shaft 14 to prevent the sterilization agent from reaching portion 18 by traveling from the top of indicator apparatus 10 down the space between outer shaft 12 and inner shaft 14.

As shown in the FIGURE, in order to use the invention, indicator apparatus 10 is inserted within the container to be sterilized so that the portion 18 of indicator apparatus 10 extends into the approximate center of the container. The container is then exposed to a sterilization process. The only way that the sterilization agent which fills chamber can reach the indicator contained in portion 18 is by entering the container, flowing over its contents and permeating septum 16 of outer shaft 12.

Following the sterilization cycle inner shaft 14 is withdrawn from outer shaft 12. Inner shaft 14 can be placed in and withdrawn from outer shaft 12 without exposing the contents of the sterilized container to the environment or the operator to the contents and without contaminating the indicator so that if, for example, the container contains biohazard waste, the sterility of the interior of the container can be determined safely. In addition, outer shaft 12 can be disposable so that, if desired, outer shaft 12 can be discarded along with the sterilized container.

Once inner shaft 14 is withdrawn from outer shaft 12 portion 18 of inner shaft 14 can be removed from inner shaft 14 so that the indicator may be observed. If the indicator is a biological one, it may have to be incubated for a period of time. Inner shaft 14 can then be fitted with a new portion 18, placed in a new outer shaft 12 and used again.

What is claimed is:

1. Apparatus for providing an indication as to whether the contents of a container have been sterilized during a sterilization process wherein the sterilization agent enters the container and comes into contact with its contents comprising:
   a first member, said first member having means for coacting with the sterilization agent to indicate the sterility of the contents of the container;
   a second member, said second member adapted to extend into the interior of the container to be sterilized, and adapted to receive and releasably engage said first member in a sealed relationship so that said coacting means of said first member can be positioned within the interior of the container to be sterilized during the sterilization process and so that said first member can be placed in and withdrawn from said second member without exposing the operator to the contents of the container or the contents of the container to the surrounding environment, at least a portion of said second member being selectively permeable to the sterilization agent so that the sterilization agent can come in contact with said coacting means of said first member without said coacting means being contaminated by the container contents; and
   means positioned between said first and second members for effecting said sealed relationship and for preventing the sterilization agent from coming in contact with said coacting means of said first member unless the sterilization agent has first permeated said second member.

2. Apparatus as recited in claim 1 wherein said first member is an elongated cylindrical shaft having said coacting means disposed at its lower end.

3. Apparatus as recited in claim 2 wherein said coacting means is releasably secured to said first member so that said coacting means may be removed from said first member for observation and said first member may be fitted with another said coacting means placed within another second member and used again.

4. Apparatus as recited in claim 1 wherein said second member is an elongated cylindrical shaft having a bore therethrough for receiving said first member and a septum disposed at its lower end that is selectively permeable to the sterilization agent.

* * * * *